United States Patent [19]

Bronstein et al.

[11] Patent Number: 5,783,381
[45] Date of Patent: Jul. 21, 1998

[54] CHEMILUMINESCENT 1,2-DIOXETANES

[75] Inventors: Irena Bronstein, Newton; Brooks Edwards, Cambridge; Alison Sparks, North Andover; John C. Voyta, Sudbury, all of Mass.

[73] Assignee: Tropix, Inc., Bedford, Mass.

[21] Appl. No.: 545,174

[22] Filed: Oct. 19, 1995

[51] Int. Cl.$^6$ ............................................. C12Q 1/00
[52] U.S. Cl. ............................. 435/4; 435/6; 435/975
[58] Field of Search ........................ 435/6, 4, 21, 25, 435/975; 549/16, 510, 221; 548/110; 362/34; 252/700, 186; 240/2.25; 540/1

[56] References Cited

U.S. PATENT DOCUMENTS

| | | | |
|---|---|---|---|
| 3,539,794 | 11/1970 | Rauhut | 240/2.25 |
| 3,576,987 | 5/1971 | Voight et al. | 240/2.25 |
| 3,597,362 | 8/1971 | Bollyky | 252/186 |
| 4,193,109 | 3/1980 | Heffernan et al. | 362/34 |
| 4,508,642 | 4/1985 | World | 252/700 |
| 4,814,949 | 3/1989 | Elliot | 362/34 |
| 4,857,652 | 8/1989 | Schaap | 549/10 |
| 4,931,223 | 6/1990 | Bronstein et al. | |
| 4,931,569 | 6/1990 | Edwards et al. | |
| 4,952,707 | 8/1990 | Edwards et al. | 549/221 |
| 4,956,477 | 9/1990 | Bronstein et al. | |
| 4,959,182 | 9/1990 | Schaap | 252/700 |
| 4,962,192 | 10/1990 | Schaap | 536/18.1 |
| 4,978,614 | 12/1990 | Bronstein | 435/21 |
| 5,089,630 | 2/1992 | Bronstein et al. | |
| 5,112,960 | 5/1992 | Bronstein et al. | |
| 5,132,204 | 7/1992 | Urdea et al. | 435/4 |
| 5,145,772 | 9/1992 | Voyta et al. | 435/4 |
| 5,220,005 | 6/1993 | Bronstein | |
| 5,270,164 | 12/1993 | Anderson et al. | 435/6 |
| 5,326,882 | 7/1994 | Bronstein et al. | 549/16 |
| 5,330,900 | 7/1994 | Bronstein et al. | |
| 5,336,596 | 8/1994 | Bronstein et al. | 435/6 |
| 5,393,469 | 2/1995 | Akhavan-Tafti | 252/700 |
| 5,438,146 | 8/1995 | Schaap et al. | 548/110 |
| 5,439,617 | 8/1995 | Akhavan-Tafti | 252/700 |
| 5,538,847 | 7/1996 | Bronstein et al. | 435/6 |
| 5,543,295 | 8/1996 | Bronstein et al. | 435/6 |
| 5,547,836 | 8/1996 | Bronstein et al. | 435/6 |
| 5,582,980 | 12/1996 | Bronstein et al. | 435/6 |
| 5,591,591 | 1/1997 | Bronstein et al. | 435/7.4 |
| 5,607,625 | 3/1997 | Wang et al. | 252/700 |
| 5,654,154 | 8/1997 | Bronstein et al. | 435/6 |

*Primary Examiner*—John Kight
*Assistant Examiner*—Dameron Jones
*Attorney, Agent, or Firm*—Oblon, Spivak, McClelland, Maier & Neustadt, P.C.

[57] ABSTRACT

Dioxetanes that can be triggered by bases are provided which can be used to detect bases in organic solvents, aqueous preparations and detect gaseous bases in the atmosphere. The dioxetanes can be used to detect the release of bases from various labels, as a means to detect the presence of a base released by physical or natural processes, to calibrate light measuring apparatus and to determine the amount of reducing or oxidizing agent present in the base.

29 Claims, 3 Drawing Sheets

CHEMILUMINESCENT 1,2-DIOXETANES

BACKGROUND OF THE INVENTION

1. Field of the Invention

This invention pertains to chemiluminescent dioxetanes which can be caused to chemiluminesce by the presence of a chemical (non-enzymatic) triggering agent, which triggering agent may either be a substance whose detection or quantification is sought, or reporter molecule associated with the presence of the sought target compound or agent. Specifically, dioxetanes of improved chemiluminescent properties, including improved quantum yield and reaction kinetics are provided which can be used in a variety of new assays, also embraced by this invention.

2. Background of the Invention

Increasing attention has been focused on 1,2-dioxetanes as chemiluminescent "reporter" molecules for use in a variety of assays. Such compounds, and their preparation in purified form, are the subject of U.S. Pat. No. 4,931,569. An early commercial compound of this type is 3-(2'-spiroadamantane)-4-methoxy-4-(3"-phosphoryloxy)-phenyl-1, 2-dioxetane disodium salt, generally identified as AMPPD, and available from Tropix, Inc. of Bedford, Mass. A variety of assays have been identified for compounds of this type, including the multi-analyte assay of U.S. Pat. No. 4,931,223, also assigned to Tropix, Inc. Use of these compounds to generate a chemiluminescent signal which is easily detected, and/or quantified, can be improved by the incorporation in the assay of "enhancer" compositions, as is specifically addressed in U.S. Pat. No. 4,978,614 and extensively disclosed in U.S. Pat. No. 5,330,900, also commonly assigned herewith. Typically, these enhancement agents have a quaternary onium salt structure, such as (vinylbenzyltributylammonium chloride) and poly (vinylbenzyl tributylphosphonium chloride) as well as the corresponding phosphonium and sulfonium salts and can form hydrophobic regions or areas within an aqueous environment, to enhance chemiluminescence.

Commercially developed dioxetanes can be generally represented by the stuctural formula:

As noted, amoung the "first generation" dioxetanes commercially developed, $Y^1, Y^2$, and Z are hydrogen, and R is a methyl group. In AMPPD, X is a phosphate group, while other "first generation" dioxetanes have also been developed and disclosed, wherein X is a different group which can be cleaved by an enzyme. Potential identities for X are well known, and include as well as phosphate, acetate, various galactosides and glucuronides and in general, any group susceptible to cleavage by an enzyme. Representative identities are set forth in Table 1 of U.S. Pat. No. 4,978,614, identified as Group Z. "Second generation" dioxetanes have been developed, disclosed and patented, wherein one or more of $Y^1$ and/or $Y^2$ of the above general Formula I have identities other than hydrogen, so as to improve chemiluminescence intensity, chemiluminescence kinetics, or both. Compounds of this type bear an active substituent on the spiroadamantyl group, that is, at least one of $Y^1$ or $Y^2$ is a group other than hydrogen. In an embodiment characteristic of this "second generation" either bridgehead carbon bears a chlorine substituent (CSPD). A wide variety of other active substituents are set forth in U.S. Pat. No. 5,112,960 and other patents assigned to Tropix, Inc. Instead of a chlorine substituent, the adamantyl ring may bear a methylene substituent, as recited in claim 1 of U.S. Pat. No. 5,326,882, to Tropix, Inc.

U.S. Pat. No. 5,326,882 also discloses and claims "third generation" trisubstituted phenyl compounds, that is, dioxetanes of the structure set forth above, wherein each of $Y^1$ and $Y^2$ may be either hydrogen or an active group, and the phenyl ring bears in addition to the enzyme cleavable group linked to the phenyl through an oxygen atom, an electron active substituent which influences enzyme kinetics and/or chemiluminescence intensity. This electron active group, Z in the above Formula, can either retard or accelerate the chemiluminescence obtained. Chemiluminescence is produced after the cleavage of the enzyme-cleavable X group of general Formula I by admixing or combining a suitable dioxetane with a corresponding enzyme specific for the X moiety. This can be accomplished in an aqueous sample, as discussed above, or on a membrane or other solid support. Membranes and similar solid supports can be optimized for increased chemiluminescent signal intensity and sensitivity or detection, by providing a polymeric membrane as disclosed in U.S. Pat. No. 5,336,596 to Tropix, Inc.

The dioxetanes described above are specifically prepared for use in connection with enzymatic assays. Thus, the X substituent, whose removal induces decomposition and chemiluminescence, is specifically designed to be removed by an enzyme. The enzyme may be the target analyte in the sample inspected, or it may be a reporter molecule attached to a probe, antigen or antibody, or any member of a specific binding pair, to detect the presence of the other member of the specific binding pair. Assay formats of this type are well known, the dioxetane chemiluminescence allowing the assay to be improved such that highly efficient, precise and sensitive detection of specific targets can be achieved.

It is also possible to select X such that it is not susceptible to removal by an enzyme, but can be removed by a specific family of chemicals. U.S. Pat. No. 4,956,477 describes various synthesis methods to prepare a wide family of dioxetanes of general Formula 1, wherein X can either be an enzyme-cleavable group, or a chemically cleavable group, such as a hydrogen atom, an alkanoyl or aroylester, an alkyl or aryl silyloxy or similar groups. Compounds of this type are also described in U.S. Pat. No. 4,962,192, Schaap, wherein the moiety X of general Formula I can be either cleavable by an enzyme or removed by a chemical. In its simplest form, X is hydrogen, whose departure can be triggered by a wide variety of "activating agents", among the simplest of which is sodium hydroxide. Because the decomposition reaction produced by the removal of the cleaving group X produces light through the decomposition of O—O bond of the dioxetane ring, to produce two carbonyl-based compounds, where the activating group is a chemical, only one photon of light can be produced per molecule of activating agent. This should be contrasted with the enzyme-triggerable dioxetanes discussed above, wherein the enzyme, as a catalyst, triggers the decomposition of many dioxetane molecules present as substrates. This catalytic multiplying effect has led to the commercial development and acceptance of enzyme-triggerable dioxetanes, while chemically-triggerable dioxetanes (herein chemically-triggerable shall refer to compounds which can be triggered stoichiometrically by chemicals, not enzymes) have not met with commercial acceptance.

Nonetheless, those of skill in the art continue to search for dioxetane compounds whose readily detectable and quanti- fiable chemiluminescent signal can be used to detect the presence of material not conveniently bound to an enzyme, or easily prepared in an aqueous assay or on a solid support.

Additionally, the use of enzymes desirable as triggering agents for enzyme-triggerable dioxetanes poses a problem in calibration of luminometers or other light sensing devices to be used in conjunction with chemiluminescent assays. In certain circumstances, it can be difficult to obtain a precise calibration with known concentrations of reagents.

Accordingly, it remains an object of those of skill in the art to obtain dioxetanes which give adequate chemiluminescence, with appropriate emission kinetics, and which are triggerable by activating agents other than enzymes, such that they can be used outside of aqueous or solid support/aqueous systems, or in assays wherein enzyme labeling is difficult or inappropriate.

SUMMARY OF THE INVENTION

The above object, and others made clear by the discussion set forth below, is met by a new family of dioxetanes which can be triggered to decompose and chemiluminesce by bringing them into contact with chemical triggering agents, including those conventionally taught with related dioxetanes described in the literature addressed above. The dioxetanes are of the structure set forth in general Formula II or Formula III below, wherein at least one of $Y^1$, $Y^2$ and Z (one, two or three maybe present) (general Formula II) is an electron active group, and where, in general Formula III, one or more of $Z^1$ and $Z^2$ is an electron-active group and the other is hydrogen, and one of $A^1$ or $A^2$ is OX with the other being hydrogen. Preferably, the non-hydrogen $A^1$ or $A^2$ is at a point of attachment to the naphthyl ring in relation to the ring's point of attachment to the dioxetane ring, such that the total number of ring atoms separating these points of attachment, including the ring atoms at the points of attachment, is an odd whole number, in a fashion analogous to the substitution pattern disclosed in U.S. Pat. No. 4,952,707.

Preferred identities for $Y^1$ and $Y^2$ include hydrogen, hydroxyl, halo and alkyl, and preferred identities for R include alkyl, aryl, cycloalkyl or cycloaryl, preferably having 1–20 carbon atoms. The R group may be unsubstituted, or substituted with 1–3 halo moieties, 1–3 alkoxy moieties of 1–3 carbon atoms each, hydroxy, amide moieties, or other moieties specifically selected to improve solubility considerations, such as carboxy or sulfoxy groups.

X is selected to be a chemically triggerable moiety, that is, one which can be removed by addition of a chemical trigger. Exemplary identities for X include hydrogen, and in general, X is removed by an activating agent which may be an acid, base or salt. In addition to hydrogen, the identity of X can be such that, when considered together, OX is alkanoyl esters, aryl esters, alkylsilyloxy, arylsilyloxy or aralkylsilyloxy.

Chemically triggerable dioxetanes of this type, exhibiting enhanced quantum yield and enzyme kinetics due to the presence of one or more electron active substituents $Y^1$, $Y^2$ and Z, can be advantageously used as calibration compounds for calibration of light measuring instruments. They may also be suitably deposited on a support for determination of the presence, in an atmospheric sample, of a gaseous base. The breakdown kinetics of these compounds are also affected by the presence of reducing agents and oxidizing agents in an aqueous sample to be analyzed. The development of these dioxetanes offers, for the first time, real and substantial commercial opportunities for the exploitation of chemically triggerable dioxetanes.

DETAILED DESCRIPTION OF THE INVENTION

Compounds of the general Formula II, and corresponding to general Formula III, have been developed with the chemiluminescent and decomposition kinetic characteristics necessary for specific applications and utilities described more in detail below. The dioxetanes of this invention are generally spiroadamantyl, aryl dioxetanes, wherein the aryl group is either a phenyl or naphthyl moiety. Although other aryl groups can be employed, selection of the aryl moiety is defined dependent on the intensity, and wavelength of emission desired in the resulting system. In general, phenyl and naphthyl dioxetanes offer superior properties.

In general Formula II:

$Y^1$ or $Y^2$, if not hydrogen, is preferably selected as a group including hydroxyl groups, a halo substituent, (preferably Cl or F, although bromine and iodine can be used), an unsubstituted lower alkyl group (herein lower alkyl refers to C1–20 carbon atoms), a hydroxy (lower) alkyl group, a halo (lower) alkyl group, a phenyl group, a halophenyl group, an alkoxyphenyl group, a hydroxyalkyl group, a cyano group or an amide group. Particularly preferred species include halo substituents, notably chlorine. While both $Y^1$ and $Y^2$ may be hydrogen if Z is not hydrogen, preferred embodiments include those wherein at least one of $Y^1$ and $Y^2$ is not hydrogen.

R is most preferably methyl or ethyl. R can also be alkyl, aryl, aralkyl, alkaryl, heteroalkyl, heteroaryl, cycloalkyl or cycloheteroalkyl, generally of 1–20 carbon atoms, in each case where R contains a heteroatom, said heteroatom is O, N or S, and most preferably a straight chain or branched alkyl group having 1–7 carbon atoms, a straight or branched hydroxyalkyl group have 1–7 carbon atoms wherein said groups may bear substituents, including 1–3 halogens, such that R may bear a trifluoroalkyl, hydroxyamide, etc. Additionally, the R group may be substituents designed to improve solubility of the overall dioxetane, for use in aqueous assays, or where particular buffers pose significant solubility problems. Examples of solubility enhancing groups include carboxylic acid moieties, sulfonic acid moieties, ethane sulfonic acid, quaternary ammonium and phosphonium salt groups such as trialkyl ammonium halide, and groups of related solubilities.

Z can be any electron-active substituent that does not suppress the chemiluminescent behavior of the dioxetane. 1, 2 or 3 Z groups may be present (as well as 1–3 $Z^1$ or $Z^2$ groups in general Formula III). These may each have the same or different identity, within the groups described. Each Z can be selected from many of a wide variety of identities. Preferred electron-active substituents include chloro, fluoro, alkoxy, aryloxy, trialkylammonium, trialkylphosphonium, alkylamido, arylamido, arylcarbamoyl, alkylcarbamoyl, cyano, nitro, ester, alkyl or arylsulfonamido, trifluoromethyl, aryl, alkyl, trialkyl-, triaryl- or alkylarylsilyl, alkyl or arylamidosulfonyl, alkyl or aryl sulfonyl and alkyl or arylthioethers. The size or number of the Z substituent is generally limited only by solubility concerns. Where reference is made to alkyl moieties, the moieties should have 1–12 carbon atoms. Suitable aryl moieties include phenyl and naphthyl as exemplary moieties. Particularly preferred species include chloro and alkoxy.

In general Formula III:

$Y^1$ and $Y^2$ have the same identities given above, and $Z^1$ or $Z^2$ has the same value as Z set forth above. Similarly, the identities for R are the same.

In general Formula II, the identity for X, and in general Formula III, the identity for $A^1$ and $A^2$ (OX) is selected such that X is easily removed by addition of a chemical triggering agent. X is preferably selected from the group including hydrogen, trialkylsilyl, triarylsilyl, arylalkylsilyl, as well as other groups that can be removed by addition of a chemical triggering agent, generally a base, or an appropriate salt. A preferred embodiment for X is hydrogen, which can easily be removed by the addition of a base, such as ammonium or sodium hydroxide.

Exemplary dioxetanes include:

3-(methoxyspiro[1,2-dioxetane-3,2'-(5-chloro)tricylo[3.3.1.1$^{3,7}$]decan]-4-yl)-6-chlorophenol 3-(methoxyspiro{1,2-dioxetane-3,2'-(5'-chloro)tricylo[3.3.1.1$^{3,7}$]decan}-4-yl)phenol These dioxetanes may be used either alone, on a solid support, or in an aqueous solution, or in the presence of water soluble quaternary polymers which sequester the substantially water insoluble dioxetanes described above (phenols), which simultaneously enhance the emission of the chemiluminescent signal. Exemplary water soluble quaternary polymers are disclosed in U.S. Pat. Nos. 5,336,596 and 5,145,772, which are incorporated herein by reference. Synthesis of the dioxetanes can be affected according to established synthetic procedures, and the synthesis does not constitute an aspect of the invention per se. The synthesis of the phenol dioxetanes of this invention is set forth for the benefit of the reader.

SYNTHESIS OF PHENOL DIOXETANES

Syn and anti 3-(Methoxyspiro[1,2-dioxetane-3.2'-(5-chloro)tricyclo[3.3.1.1$^{3,7}$]decan]-4-yl)-6-chlorosphenol 1.

3-(Methoxy-5-chlorotricyclo[3.3.1.1$^{3,7}$]dec-2-ylidenemethyl)-6-chlorophenol (504.6 mg, 1.49 mmol) was dissolved in hplc-grade acetonitrile (8 ml). Pyridine (30 μl, 0.371 mmol) and 5,10,15,20-tetraphenyl-21H,32H-porphine (TPP, 0.5 ml of a 2 mg TPP/ml CHCl$_3$) were immediately added and the solution was stored on ice. After setting aside an aliquot for tic analysis, the solution was saturated with oxygen at 0° C. while a 400 W high pressure sodium vapor lamp warmed for 10 min. The solution was photooxygenated at 0° C. for 30 min while passing oxygen through it. Tic analysis (elution of reaction and starting solutions in 20% EtOAc:hexanes twice, followed by thermolysis or phosphomolybdic acid stain on a hot plate) indicated clean oxidation to a mixture of two dioxetanes. The solvent was removed by rotary evaporation, followed by high vacuum with no heat. The resulting pink oil was loaded onto a hexanes-flushed silica gel column, eluted with hexanes until the pink eluate was removed and then eluted with 2–4% EtOAc:hexanes to recover the dioxetanes. The light pink dioxetane fractions were combined, evaporated to an oil under vacuum with no heat and stored overnight in the freezer which gave white crystals in solution. After removing the mother liquor, the crystals were triturated once with 10% EtOAC and three times with hexanes to yield white crystals of one dioxetane isomer (174 mg, 32%, mp 134° C). The mother liquor was loaded onto a hexanes-flushed silica gel column and eluted as described above. The dioxetane fractions were collected and evaporated under vacuum at room temperature to yield a dioxetane mixture as a clear oil (196 mg, 35%).

$^1$H NMR (dioxetane crystal [one isomer], CDCl$_3$, ppm): 0.98 (1 H, d, J=14 Hz), 1.21 (1H, d, J=15 Hz), 1.73–2.30 (10H, m), 3.18 (1H, broad s), 3.20 (3H, s), 5.68 (1H, s), 7.0–7.2 (1H, very broad signal), 7.37–7.40 (2H, m)

$^1$H NMR (dioxetane isomer mixture, CDCl$_3$, ppm): 0.98 (1H, d), 1.2 (1H, d), 1.40–2.43 (22H, m), 3.18 (2H, broad s), 3.19 (3H, s), 3.20 (3H, s), 5.73 (1H, s), 5.76 (1H, s), 7.0–7.2 (2H, very broad signal), 7.38–7.41 (4H, m)

Syn and anti 3-(Methoxyspiro[1,2-dioxetane-3.2'-(5-chloro)tricyclo [3.3.1.1$^{3,7}$]decan]-4-yl)phenol 2.

This dioxetane mixture was synthesized as described above.

$^1$H NMR (dioxetane isomer mixture, CDCl$_3$, ppm): 0.90–2.34 (24H, m), 3.19 (2H, broad s), 3.206 (3H, S), 3.213 (3H, s), 5.30 (1H, s), 5.35 (1H, s), 6.86–7.32 (8H, m)

APPLICATIONS

The above-described chemically-triggerable dioxetanes are suitable for a wide variety of applications for chemiluminescent detection and/or quantification of the presence of a target element as desired.

As noted at the outset, it is sometimes difficult to calibrate luminometers or other light measuring instruments using enzymatically triggered dioxetanes, because the catalytic "turnover" effect of enzymes. As the- dioxetanes of this invention will give a precise amount of light (certain number of photons) for a certain number of molecules, light measuring instruments can be easily calibrated using the dioxetanes of this invention. Thus, a light measuring instrument is provided with a tube or other container containing a pre-measured amount of a chemically triggered dioxetane of this invention. A second container of a pre-measured amount of a corresponding chemical triggering agent, such as sodium hydroxide, is provided. The contents of the tubes are mixed and placed in an instrument which measures relative light units. The resulting number can be used to normalize the experimental data obtained from the measuring instrument manually, or stored automatically into the instrument which would also calculate the experimental results, using the stored correction factor. In this way, light measuring instruments may be "tared".

Figure 1:
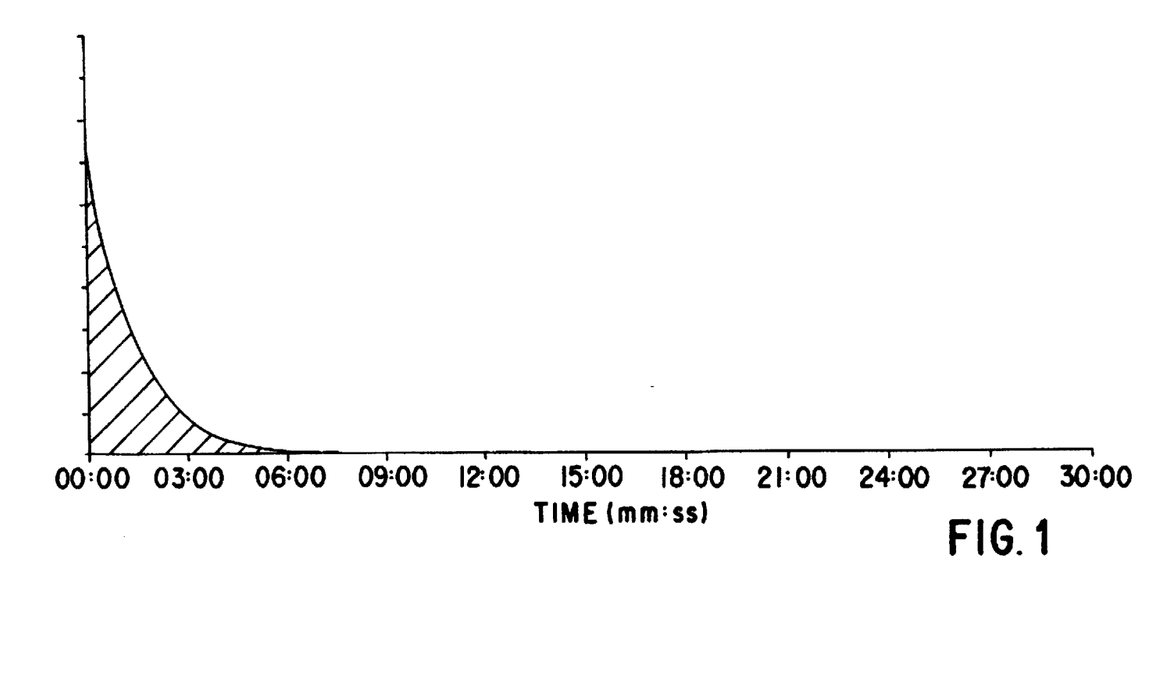
FIG. 1 is the recorded chemiluminescent signal for 3-(4-methoxyspiro[1,2-dioxetane-3,2'-(5'-chloro)tricyclo [3.3.1.1$^{3,7}$]-decan]-4-yl]phenol (CSHD) triggered by diethanolamine.
Figure 2:
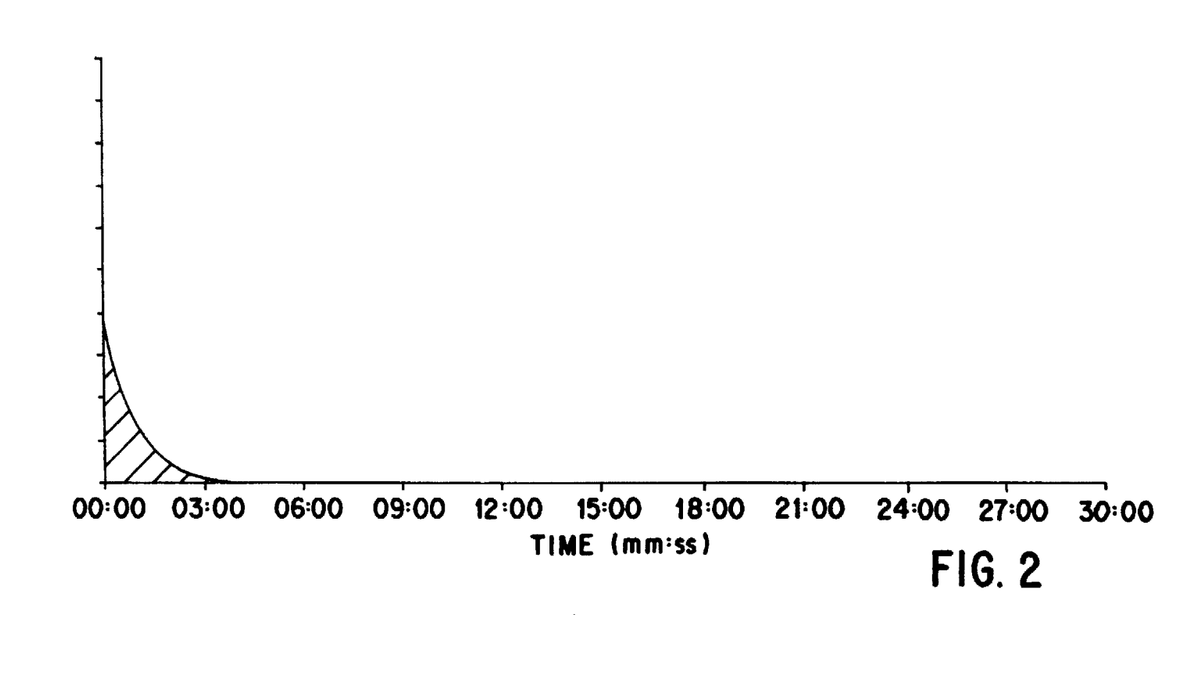
FIG. 2 is the recorded chemiluminescent signal of 3-(methoxyspiro [1,2-dioxetane-3,2'-(5-chloro)trycyclo [3.3.1.1$^{3,7}$]decan]-4-yl)-6-chlorophenol (CDH-Star) triggered by diethanolamine.

In this respect, the dioxetanes of this invention have a characteristic and measurable signal. The chemiluminescent signal intensity of CSHD and CDH-Star was measured according to the following protocol: 4 μL of a 25 mM stock solution of the dioxetane in acetonitrile was added to 0.496 mL of 0.1 M diethanolamine at 30° C. in a Turner model 20e luminometer (with a 1.0 neutral density filter inserted in front of the photomultiplier tube), and the chemiluminescent signal was recorded. The recorded chemiluminescent signal intensities for CSHD and CDH-Star appear as FIGS. 1 and 2, respectfully.

Figure 3:
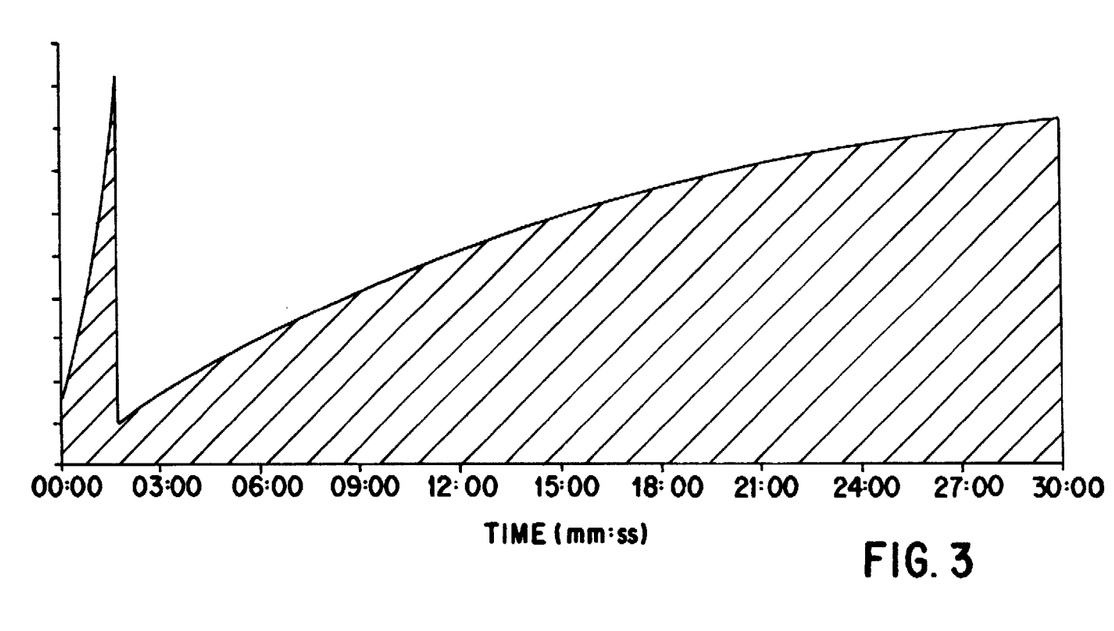
FIG. 3 is the chemiluminescent signal obtained by exposing CSHD dried on a nylon membrane to an atmosphere including ammonia as a gaseous base.

Importantly, the dioxetanes of this invention can also be used to demonstrate the presence of a gaseous base, that is, which dispenses with an aqueous assay format entirely. To demonstrate the sensitivity of this procedure, 4 μL of a 25 mM dioxetane stock solution in acetonitrile, was dried onto a 7 mm×7 mm square piece of nylon membrane (Pall Biodyne A). The membrane was then inserted into a 12×75 mm glass tube. A microtiter well (Dynatech) was then placed with a piece of wire approximately 30 mm into the top of the tube. A 50 μL aliquot of 0.3% ammonium hydroxide was then added into the microtiter well, the tube was sealed with paraffin, inserted into a Turner model 20e luminometer (with a 3.0 neutral density filter in front of the photomultiplier tube), and the chemiluminescent signal was recorded. The results are shown in FIG. 3. In this experiment, the glowing blue membrane was easily observed with a naked eye.

The detection of gaseous bases such as ammonia is useful in a wide variety of applications. These include air monitors for livestock buildings and flues, as well as line monitors for various commercial environments in which ammonia is present as a contaminant or by-product. Additionally, a wide variety of assays rely on the production of ammonia or ammonia gas as a "reporter entity" for the presence of a particular target compound. As one example, the presence and concentration of glutamic acid and its corresponding salt, glutamate are of importance to the food industry, bioreactors and biomedical research. Application of this invention to these fields provides a simple and effective glutamate monitor. Such applications detect ammonia gas produced by the enzymatic deamination of a target substrate. Glutamate oxidase will convert glutamate, in the presence of oxygen, to the corresponding α-ketoglutarate with the generation of ammonia. Similarly, glutamate dehydrogenase will convert glutamate in the presence of NAD$^+$ to α-ketoglutarate with the generation of ammonium ion and NADH. The ammonia generated can be detected through the claimed invention, according to the Example set forth above.

Detection of ammonia as a by-product of reactions involving target analytes is common to a wide range of endeavors. As noted, the claimed invention can detect ammonia as well as other bases in both liquid and gaseous form. This frequently involves release of ammonia due to enzymatic action. Urea is both a target analyte, and a label for other target analytes. Thus, urea concentration in blood samples is an important element of patient monitoring, and the corresponding enzyme, urease, converts urea with the release of ammonia. Urease is also used as an enzyme-label where urea is used as a substrate. DNA contamination in bioreactors presents a recognized commercial problem. DNA contamination may be quantified by detection of captured ssDNA, and with a urease-conjugated anti-DNA monoclonal antibody. Presence and degree of concentration of the contaminating DNA is detected by the presence of ammonia released by the reaction of the urease enzyme label on urea added to, or present in, the process mixture. The detection may be either of gaseous ammonia, or ammonia in the aqueous preparation.

Ammonia is also generated by the activity of creatinine imminohydrolase on creatinine. Creatinine, a product of metabolism, is the target of assays performed through the use of several kits commercially available. The invention is not, however, limited to bioassays. In addition to the glutamate and urease-based assays discussed above, the detection of organonitrile contaminants in environmental samples can be detected through the release of ammonia caused by enzymatic hydrolysis of benzonitriles.

In addition to the above-described assays, a wide variety of other assays are embraced by the claimed invention. Applicants note, in passing, that the invention resides in the quick, easy and, if desired, quantitative detection of the presence of the target analyte using the dioxetanes of the claimed invention. Sensors and assays, per se, for targets of the above are known, using other measures. Fiber-optic biosensors, including glutamate biosensors, are described by Arnold, "Fiber-Optic-Based Bio-catalytic Biosensors, Chemical Sensors and Microinstrumentation", ACS Symposium Series, No. 403, 1989, as well as *Anal. Chem.* 1992, 64:1051–1055. Sensors which detect ammonia through other processes are also described in *Scientific American* (August) 1991, pp. 64–69, as well as elsewhere.

The specific apparatus used to detect the chemiluminescence produced in the assays of this invention is not limited.

Any of a wide variety of well-known light-detection instruments and accessories can be used. Representative devices include photomultiplier tubes, charge-coupled device (CCD) cameras, SIT cameras, photodiode arrays, photographic film (black and white, color, X-ray, standard and instant, etc.) as well as other standard devices. Any detector can be linked, where necessary, through a fiber-optic cable or waveguide, depending on the application envisaged.

Applicants also emphasize that detection of gaseous bases is not limited to ammonia. Virtually any soluble or gaseous base can be employed. The base may be soluble in either aqueous or non-aqueous systems. Suitable gaseous bases include methylamine, ethylamine, isopropylamine, t-butylamine, propylamine, allylamine, s-butylamine, isobutylamine, isopentylamine, dimethylamine, diethylamine, diisopropylamine, pyrrolidine, diethyl hydrazine, dimethyl hydrazine, trimethylamine and triethylamine. Also, cyclic and acyclic amines, and all silated amine derivatives ($R_3Si$—N). The base may also be thermally generated from any organic compound or salt such as a known trichloroacetate salt which will decompose to release said base upon heating.

These dioxetanes, because of their particular reaction kinetics, can also be used to test for the presence of reducing and oxidizing agents in a sample. Again, not only detection, but quantification of the amount of agent present can be achieved. For example, the kinetics of breakdown of CDH-Star or other dioxetane of the invention is accelerated dramatically by low concentrations of reducing agents such as dithiothrietol (DTT) and β-mercaptoethanol. This effect is neutralized by oxidizing agents such as $H_2O_2$. Based on this information, an assay for the detection of reducing agents in a sample can be designed as follows: add an aliquot of the sample to be tested to a solution of CDH-Star in 0.1 M diethanolamine or other buffer, 1 mg/mL Sapphire II polymer or other enhancement agent as desired and determine the $t_{1/2}$ of the chemiluminescent signal. A reduction in the $t_{1/2}$ would be proportional to the amount of reducing agent in the sample. Furthermore, an assay for the presence of oxidizing agents could be designed as follows: add an aliquot of the sample to be tested to a solution of CDH in 0.1M diethanolamine or other buffer, 1 mg/mL Sapphire II polymer or other enhancer, 1 mM DTT or similar reducing agent, and determine the $t_{1/2}$ of the chemiluminescent signal. An increase in the $t_{1/2}$ would be proportional to the amount of oxidizing agent in the sample.

As noted, sensitivity, and quantum yield can be improved by the addition of water soluble polymers to aqueous assays. Similarly, assays performed on a membrane or other solid support can be improved, in terms of sensitivity by using a polymer coated membrane which provides "micro environments" that are substantially hydrophobic. The presence of water tends to "quench" the light-releasing reaction of the dioxetanes. Use of hydrophobic enhancements initially established for use in connection with enzyme-triggerable dioxetanes as discussed above can be similarly employed in connection with the invention of this application.

The dioxetanes of this invention may also be used in non-assay applications. Currently, American Cyanamid Company produces and sells a chemiluminescent device generally marketed and referred to as a "light stick", and is available from Cyanamid under the mark Cyalume®. The light sticks are popular for those away from conventional sources of electrical illumination, including campers, boaters, and the like. The currently available product is, essentially, a translucent or transparent plastic tube or flexible "stick", which is provided with a rupturable membrane.

When one wishes to activate the "light stick", the stick is bent or hit against an unyielding surface with mild force to rupture the membrane, which provides for intermixing of the chemiluminescent compound and the agent inducing chemiluminescence.

A major limitation on the commercially available products of this type is that the chemiluminescence persists for no more than twelve hours. Frequently, sustained illumination devices, lasting for more than twelve hours, indeed, more than a day or two, are desirable or necessary.

The dioxetanes of general Formula II and III can, by specific selection of the identity of each Z or $Z^1$, $Z^2$, can be provided with a sufficiently long $T_{1/2}$ such that chemiluminescence can be sustained for a period in excess of twelve hours including periods up to and in excess of a day or more. The physical structure of the light stick of this invention is not dissimilar from those currently available on the market place. Thus, a transparent or translucent container, generally in the form of a tube or stick, is provided with a rupturable membrane. The membrane divides the hollow interior of the tube into two chambers. In one chamber is a predetermined amount of the selected dioxetane, in a suitable solvent. Since the solvent system need not be aqueous, and the dioxetanes of this invention are characteristically more highly soluble in an organic solvent, simple solvent systems may be used. The other chamber contains the base or salt chemical trigger. The base is provided either in liquid form, or dissolved in a liquid which is at least miscible with, if not soluble in, the solvent for the dioxetane. Upon bending the light stick, the chemiluminescent decomposition of the dioxetane is initiated by admixture of the base triggering agent and the dioxetane, which chemiluminescence will persist over the extended life of the light stick. As the materials necessary for use are neither toxic nor environmentally dangerous, use of these illumination devices even by those having a relatively low level of skill or experience in sustained outdoor activities is safe and easy. Suitable dioxetanes will generally exhibit one or more Z groups that are electron withdrawing, such as chlorine including but not limited to the following compounds:

X = H or Cl
Y = electron-withdrawing group, e.g., Cl

X = H or Cl
Y = electron-withdrawing group, e.g., Cl

-continued

X = H or Cl
Y = electron-withdrawing group, e.g., Cl

This invention has been disclosed by reference to generic description, and specific embodiment. No example or embodiment is intended as limiting, and other identities for the various substituents, as well as detectable targets and triggers will occur to those of ordinary skill in the art without the exercise of inventive faculty, and remain within the scope of the invention, save is limited by the claims set forth below.

What is claimed is:

1. A chemically triggerable dioxetane of the Formula:

wherein X is H or (E)$_3$Si, wherein each E is C$_{1-12}$ alkyl or C$_{6-12}$ aryl, wherein R is a moiety of 1–20 carbon atoms and is alkyl, aryl, aralkyl, alkaryl, heteroalkyl, heteroaryl, cycloalkyl or cycloheteroalkyl, in each case where R comprises a heteroatom, said heteroatom being O, N or S, and wherein R is unsubstituted or substituted with 1–3 halo moieties, 1–3 alkoxy moieties of 1–3 carbons each,1–3 hydroxy moieties, 1–2 amide moieties, a carboxy group or a sulfonic acid group, Y$^1$ and Y$^2$ are independently hydrogen, hydroxy, Cl, F, Br, I, unsubstituted lower alkyl, hydroxy lower alkyl, halo lower alkyl, phenyl, halophenyl, alkoxy phenyl, cyano or amide, Z is 1, 2, or 3 groups which are selected from the group consisting of chloro, fluoro, alkoxy, aryloxy, trialkylammonium, trialkylphosphonim, alkylamido, arylamido, arylcarbamoyl, alkylcarbamoyl, cyano, nitro, ester, alkyl or arylsulfonamido, trifluoromethyl, aryl, alkyl, trialkyl-, triaryl- or alkylarylsilyl, alkyl or arylamidosulfonyl, alkyl or aryl sulfonyl, and alkyl or arylthioethers, with the proviso that at least one of Y$^1$, Y$^2$, and Z is not hydrogen.

2. A chemically triggerable dioxetane of the Formula:

wherein one of Z$^1$ and Z$^2$ is hydrogen and the other is selected from the group consisting of chloro, fluoro, alkoxy, aryloxy, trialkylammonium, trialkylphosphonim, alkylamido, arylamido, arylcarbamoyl, alkylcarbamoyl, cyano, nitro, ester, alkyl or arylsulfonamido, trifluoromethyl, aryl, alkyl, trialkyl-, triaryl- or alkylarylsilyl, alkyl or arylamidosulfonyl, alkyl or aryl sulfonyl, and alkyl or arylthioethers, one of A$^1$ and A$^2$ is hydrogen and the other is OX, wherein X is H or (E)$_3$Si, wherein each E is C$_{1-12}$ alkyl or C$_{6-12}$ aryl, wherein Y$^1$ and Y$^2$ are independently hydrogen, hydroxy, Cl, F, Br, I, unsubstituted lower alkyl, hydroxy lower alkyl, halo lower alkyl, phenyl, halophenyl, alkoxy phenyl, cyano or amide, R is a moiety of 1–20 carbon atoms and is alkyl, aryl, aralkyl, alkaryl, heteroalkyl, *heteroaryl, cycloalkyl or cycloheteroalkyl, in each case wherein R comprises a heteroatom, said heteroatom being O, N or S, and wherein R is unsubstituted or substituted with 1–3 halo moieties, 1–3 alkoxy moieties of 1–3 carbons each, 1–3 hydroxy moieties, 1–2 amide moieties, a carboxy group or a sulfoxy group.

3. The dioxetane of claim 1, wherein at least one of Y$^1$, Y$^2$ and Z is Cl or alkoxy.

4. The dioxetane of claim 2, wherein Z$^1$ or Z$^2$ is Cl, F, alkoxy, aryloxy, trialkylammonium, alkylamido, arylamido, arylcarbamoyl, alkylcarbamoyl, cyano, nitro, alkyl- or arylsulfonamido, trifluoromethyl, aryl, alkyl, trialkyl-, triaryl- or alkylaryl-silyl, alkyl- or arylamidosulfonyl, alkyl- or arylsulfonyl and alkyl or arylthioether, wherein Z is comprised of 0–12 carbon atoms.

5. The dioxetane of claim 1, wherein X is H.

6. The dioxetane of claim 1, wherein said dioxetane is 3-(methoxyspiro[1,2-dioxetane-3,2'-(5-chloro)tricyclo [3.3.1.1$^{3,7}$]decan]-4-yl-6-chlorophenol (CDH-Star) or 3-(4-methoxyspiro[1,2-dioxetane-3,2'-(5'-chloro)tricyclo-[3.3.1.1$^{3,7}$]decan-4-yl)phenol (CSHD).

7. The dioxetane of claim 2, wherein at least one of Y$^1$, Y$^2$ and Z$^1$ or Z$^2$ is Cl or alkoxy.

8. The dioxetane of claim 2, wherein Z$^1$ or Z$^2$ is Cl, alkoxy, aryloxy, trialkylammonium, alkylamido, arylamido, arylcarbamoyl, alkylcarbamoyl, cyano, nitro, alkyl- or arylsulfonamido, trifluoromethyl, aryl, alkyl, trialkyl-, triaryl- or alkylaryl-silyl, alkyl- or arylamidosulfonyl, alkyl- or arylsulfonyl and alkyl or arylthioether, wherein Z is comprised of 0–12 carbon atoms.

9. The dioxetane of claim 2, wherein X is H.

10. A method of detecting the presence or amount of a base in a sample, comprising:

contacting said sample with a dioxetane of claims 1 or 2, and detecting any light emitted by said dioxetane, wherein the emission of light from said dioxetane corresponds to the presence of said base and the amount of light emitted corresponds to the amount of said base in said sample.

11. The process of claim 10, wherein said sample is an aqueous preparation to which said dioxetane is added.

12. The method of claim 11, wherein an enhancement agent comprising a water-soluble quaternary onium polymer is added to said sample.

13. The method of claim 11, wherein said dioxetane is provided on a surface of a membrane, said membrane surface providing hydrophobic regions wherein a dioxetane anion produced by release of X from said dioxetane is sequestered.

14. The method of claim 10, wherein said dioxetane is provided on a support, said base is gaseous in nature, and said support is suspended in the atmosphere containing said gaseous base.

15. The method of claim 14, wherein said gaseous base is generated from said sample and said atmosphere is the atmosphere surrounding said sample.

16. The method of claim 15, wherein said gaseous base is ammonia.

17. The method of claim 15, wherein said gaseous base is generated by enzymatic digestion of a substrate resulting in release of said base.

18. The method of claim 17, wherein said enzymatic digestion comprises deamination.

19. The method of claim 10, wherein said base is generated by enzymatic digestion of a substrate resulting in the release of said base.

20. The process of claim 19, wherein said substrate is selected from the group consisting glutamate, creatinine, urea and organonitriles.

21. The method of claim 20, wherein said enzymatic digestion comprises deamination.

22. A method of calibrating a light measuring instrument, comprising:

providing a sample comprising a predetermined amount of base, combining said sample with a predetermined amount of dioxetane of claims 1 or 2 such that the number of molecules of dioxetane provided is at least as great as the number of molecules of base provided, detecting the amount of light released from said sample combined with said dioxetane with said instrument, and calibrating said instrument such that the light detected thereby corresponds to the amount of light emitted by said sample contacted by said dioxetane.

23. A method of determining the presence and amount of reducing agent in a sample, comprising adding to said sample a dioxetane of claims 1 or 2 and a predetermined amount of base to generate a chemiluminescent signal, determining the $T_{1/2}$ of the chemiluminescent signal and comparing it against the $T_{1/2}$ of said dioxetane produced by said base in the absence of said sample, wherein a reduction in the $T_{1/2}$ is proportional to the amount of reducing agent present in said sample.

24. A method of determining the presence and amount of an oxidizing agent in a sample, comprising adding to said sample a dioxetane and a predetermined amount of reducing agent, and a predetermined amount of base to generate a chemiluminescent signal from said dioxetane, and measuring the $T_{1/2}$ of said chemiluminescent signal, and comparing said $t_{1/2}$ with the $t_{1/2}$ obtained from said dioxetane, base and reducing agent in the absence of said sample, wherein any increase in the $t_{1/2}$ obtained from said sample is proportional to the amount of oxidizing agent present in said sample.

25. A kit for the detection of a gaseous base, comprising:

a membrane bearing a dioxetane of claims 1 or 2 on a surface thereof, and means for detecting chemiluminescence emitting by said dioxetanes.

26. The kit of claim 25, wherein said means for detecting chemiluminescence comprises light sensitive film.

27. A chemiluminescent illumination device, comprising:

a container defining a hollow interior, which container is further comprised of a rupturable membrane dividing said hollow interior into two chambers, one said chamber containing a dioxetane of claims 1 or 2, wherein one of $Y^1$ and $Y2$ is chlorine, and the other is hydrogen, and each Z, $Z^1$ and $Z^2$ present is a electron withdrawing moiety, the other said chamber containing a base, which when admixed with said dioxetane, will induce the chemiluminescent decomposition of said dioxetane, said base being present in the form of a solution miscible with the dioxetane solution of said first chamber, wherein, upon rupture of said membrane, said dioxetane solution and said base solution are intermixed inducing decomposition of said dioxetane and chemiluminescence as a result thereof.

28. The illumination device of claim 27, wherein said container is in the form of a tube whose walls are transparent.

29. The illumination device of claim 27, wherein, upon rupturing of said membrane, said chemiluminescence persists for a period at least of twelve hours.

* * * * *